United States Patent [19]

Sato

[11] Patent Number: 5,021,140
[45] Date of Patent: Jun. 4, 1991

[54] ION-SELECTIVE ELECTRODE
[75] Inventor: Takehiko Sato, Saitama, Japan
[73] Assignee: Fuji Photo Film Co., Ltd., Kanagawa, Japan
[21] Appl. No.: 295,456
[22] Filed: Jan. 10, 1989
[30] Foreign Application Priority Data Jan. 13, 1988 [JP] Japan .................. 63-5416

[51] Int. Cl.⁵ ......................................... G01N 27/333
[52] U.S. Cl. ............................... 204/416; 204/153.13; 204/418
[58] Field of Search ............... 204/416, 418, 419, 420, 204/435, 153.13

[56] References Cited

U.S. PATENT DOCUMENTS

| 3,686,091 | 8/1972 | Sawa et al. | 204/435 |
| 3,767,553 | 10/1973 | Brown et al. | 204/296 |
| 4,236,987 | 12/1980 | Schindler et al. | 204/296 |
| 4,263,343 | 4/1981 | Kim | 204/435 |
| 4,269,682 | 5/1981 | Yano et al. | 204/435 |
| 4,272,328 | 6/1981 | Kim et al. | 204/418 |
| 4,303,408 | 12/1981 | Kim et al. | 204/418 |
| 4,349,426 | 9/1982 | Sugahara et al. | 204/418 |
| 4,505,801 | 3/1985 | Detwiler et al. | 204/418 |
| 4,783,251 | 11/1988 | Seshimoto et al. | 204/435 |

OTHER PUBLICATIONS

Partington, "An Advanced Treatise on Physical Chemistry", vol. 2, (1952), pp. 163–164.

Primary Examiner—T. Tung
Attorney, Agent, or Firm—McAulay Fisher Nissen & Goldberg

[57] ABSTRACT

An ion-selective electrode comprises a non-conductive support, an inner reference electrode and an ion-selective layer mounted in this order. A surface of the ion-selective layer is covered with a material which forms a contact angle of at least 90° with water. By this material, the surface area over which a test liquid comes into contact with the ion-selective layer is reduced.

7 Claims, 3 Drawing Sheets

F I G. 1A
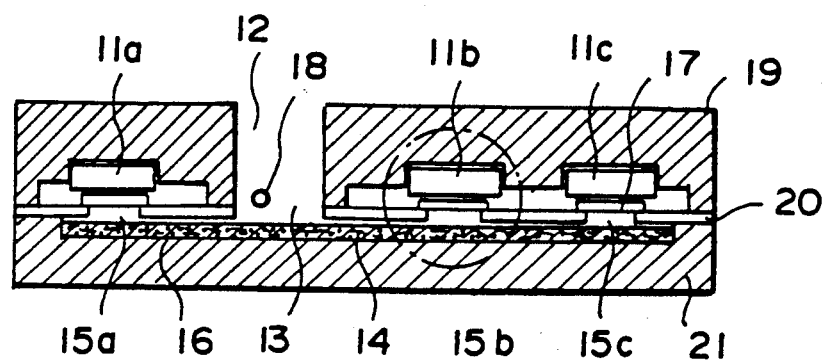
F I G. 1B
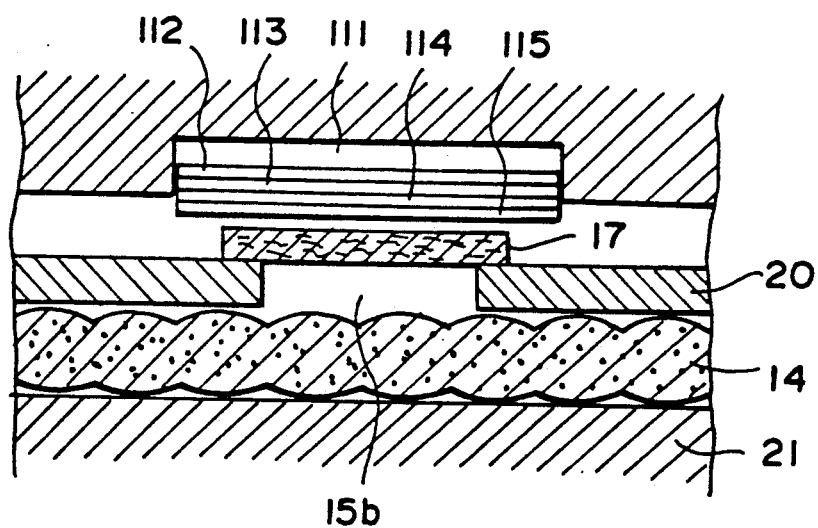

ION-SELECTIVE ELECTRODE

BACKGROUND OF THE INVENTION

1. Field of the Invention

This invention relates to an ion-selective electrode which is useful for potentiometrically determining the ionic activity level (or concentration) of a specific ion contained in an aqueous liquid, especially in the body fluids (blood, urine, saliva or the like) of an organism.

2. Description of the Prior Art

A method for determining the ionic activity level of a specific ion contained in drop of a liquid (tap water, river water, sewage, industrial drainage or the like) or in body fluids (blood, urine, saliva or the like) by using a sheet-like ion-selective electrode is known. This method is performed by spotting a test liquid and a reference liquid onto the surfaces of ion-selective layers of a pair of ion-selective electrodes. These ion-selective electrodes are electrically separated from each other. The liquids thus spotted come into contact with each other through a bridge disposed between these ion-selective electrodes so as to make electric conduction. The potential difference across the ion-selective electrodes is measured. The ionic activity level of the test liquid is determined from this measurement. A device for determining ionic activity levels by this method is disclosed in U.S. Pat. Nos. 4,053,381 and 4,273,639 and the like.

In general, an inner reference electrode which comprises a conductive layer and a slightly soluble salt Japanese Unexamined Patent Publication Nos. 56(1981)-33537 and 57(1982)-186163 is preferable. The silver chloride layer may be formed on the silver layer by electrolytic oxidation of the silver layer or vapor deposition of silver chloride. A silver bromide layer and a silver iodide layer can be formed in a manner similar to the method for forming silver chloride layer.

As the quaternary ammonium salt, which is a well-known ingredient of the halide ion-selective layer, a tetraalkylammonium salt having a long-chain alkyl group, for example, trioctylmethylammonium chloride (e.g. "Aliquat 336" produced by Aldrich Chemical Company) can be used.

In order to form the halide ion-selective layer, the quaternary ammonium salt and the polymer which is used as the binder may be dissolved in a solvent, which can dissolve them relatively well, to form a solution of appropriate concentration, and then this solution may be applied to or sprayed upon the silver halide layer (e.g. silver chloride layer) and dried.

As the binder, polyvinyl chloride or a vinyl chloride copolymer such as the one disclosed in U.S. Pat. No. 4,555,274 may be used. Also, various vinyl acetals, e.g. vinyl formal, vinyl acetal (acetal with acetaldehyde) or vinyl butyral are acceptable. In particular, vinyl butyral is preferable. As the organic polymer, a homopolymer of vinyl acetals or a copolymer of a vinyl acetal with another monomer which can be copolymerized with vinyl acetal may be used. The layer, and an ion-selective layer are essential to the sheet-like ion-selective electrode. A water-soluble salt layer is often disposed between the slightly soluble salt layer and the ion-selective layer. Usually, these layers are mounted on a non-conductive, water-impermeable support so that the ion-selective layer (or an additional layer) is the outermost layer.

A chloride ion-selective layer, in which a silver layer, a silver chloride layer and a chloride ion-selective layer containing a hydrophobic polymer as a binder are mounted in this order is well-known and is disclosed, for example, in U.S. Pat. No. 3,591,482.

In general, a halide ion-selective layer comprises a quaternary ammonium salt (e.g. "Aliquat 336" produced by Aldrich Chemical Company) and a hydrophobic organic polymer which is used as a binder. As the hydrophobic organic polymer used as the binder, ployvinyl chloride, a vinyl copolymer as disclosed in U.S. Pat. No. 4,555,274, the polyvinylacetal species disclosed in Japanese Unexamined Patent Publication No. 62(1987)-169044 or the like, are known.

However, in the ion-selective electrodes using such halide ion-selective layers, the voltage across a pair of electrodes cannot accurately reflect the ionic activity level of a halide ion unless the ion-selective layer contains a means, e.g. an attached mask, for limiting the surface area over which the liquid comes into contact with the halide ion-selective layer.

SUMMARY OF THE INVENTION

The object of the present invention is to provide an ion-selective electrode in which the ionic activity or the concentration of an ion can be accurately determined by measuring the voltage across a pair of electrodes even without means for limiting the surface area over which a liquid comes into contact with the electrode.

The ion-selective electrode in accordance with the present invention comprises a conductive layer, a slightly soluble salt layer and an ion-selective layer which are mounted in this order. The surface of the ion-selective layer is coated with a material which forms a contact angle of at least 90° with water.

In particular, a halide ion-selective electrode is formed by mounting a silver layer, a silver halide layer (e.g. a silver chloride layer) and a halide ion-selective layer in this order. The halide ion-selective layer comprises a quaternary ammonium salt (e.g. "Aliquat 336" produced by Aldrich Chemical Company) and a hydrophobic organic polymer which is used as a binder, and the surface of the halide ion-selective layer is coated with a material which forms a contact angle of at least 90° with water.

The conductive layer of the ion-selective electrode can be formed by a metal such as silver or a carbon such as carbon black. Practically, silver is used therefor. The silver layer and the silver chloride layer can be formed by various known methods. A method such as the one disclosed in examples of copolymers which may be used as a copolymer of vinyl butyral and vinyl alcohol; a copolymer of vinyl butyral and vinyl acetate; a copolymer of vinyl butyral, vinyl alcohol and vinyl acetate; a copolymer of vinyl butyral and vinyl chloride; a copolymer of vinyl butyral, vinyl alcohol, vinyl acetate and vinylmethyl ether; or the like may be used. Although the ratio of copolymerization is not limited in particular, a copolymer containing at least 50 mol % of vinyl butyral is preferable because the interference from the bromide ion is slight.

An electrolyte layer may be provided by the method disclosed, for example, in U.S. Pat. Nos. 4,214,968, 4,578,173, 4,571,293, 4,707,243 and 4,615,788 and the like.

The ion-selective electrode may have selectivity for ions other than halide ions. For example, it may have selectivity for potassium ions, sodium ions, calcium ions, carbonate ions, lithium ions, cadmium ions, or hydrogen ions. The present invention, however, is useful if the ion-selective layer is relatively hydrophilic like chloride ion-selective layer.

The support for the ion-selective electrode comprises a water-impermeable insulator. Preferably, it comprises a thermoplastic organic polymer, e.g. polyethyleneterephthalate, polystyrene or polycarbonate. Desirably, the surface of the support on which a metal layer of silver is provided is subjected to surface processing or is subbed, in order to enhance the bonding of the silver layer to the support. The same is also true in the cases where conductors other than silver are used.

The material having a contact angle of at least 90° with water is preferably a higher hydrocarbon, a higher fatty acid, a higher alcohol, a fluorocarbon compound (e.g. perfluoro fatty acid), a polysiloxane compound or the like which is a solid or semisolid at a room temperature. For example, paraffin, vaseline, stearic acid, palmitic acid, behenic acid, 2-pentadecanoic acid, 1-eicosanol, cetyl alcohol, perfluoroeicosane, perfluorolauric acid, 1,1-dihydroperfluorooctylacrylate polymer, dimethylpolysiloxane or methylhydrogenpolysiloxane may be used as this material.

This material is formed as a thin layer on the ion-selective layer. The thickness of this layer is selected such that halide ions can substantially penetrate therethrough. In general, the thickness of this layer is within the range of 0.01 to 2 m. The maximum thickness may differ from material to material.

In order to form a thin layer of this material, a solution containing a low concentration of this material may be applied to the ion-selective layer and dried.

Preferably, in order to ensure accurate measurements, the ion-selective electrode in accordance with the present invention is formed as an integral ion-selective electrode pair such as the one disclosed in Japanese Unexamined Patent Publication No. 58(1983)-156848, and the ionic activity of halide ion in a test liquid is determined based on the principle disclosed in U.S. Pat. No. 3,709,796 (King et al) and U.S. Pat. No. 3,770,608 (Kelch et al) by supplying the test liquid and a reference liquid to the respective electrodes.

The ion-selective electrode pair may be formed by the method disclosed in Japanese Unexamined Patent Publication Nos. 58(1983)-102146 and 60(1985)-243555.

The ion-selective electrode in accordance with the present invention may be used in various ways. For example, it may be used in the devices for determining ionic activity which are disclosed in U.S. Pat. No(s). 4,437,970, 4,684,445 and 4,789,435; Japanese Unexamined Utility Model Publication Nos. 62(1987)-111655, 62(1987)-152256 and 62(1987)-152257; Japanese Unexamined Patent Publication Nos. 62(1987)-157561, 62(1987)-157562 and 63(1988)-151845; and Japanese Patent Application No. 62(1987)-205626. Devices having at least two pairs of such ion-selective electrodes are practically advantageous since the ionic activities of different ions can be determined simultaneously.

BRIEF DESCRIPTION OF THE DRAWINGS

FIG. 1A is a cross sectional view taken along line X—X in FIG. 1, FIG. 1B is an enlarged view of the circled portion in FIG. 1A.

DESCRIPTION OF THE PREFERRED EMBODIMENTS

Figure 1:
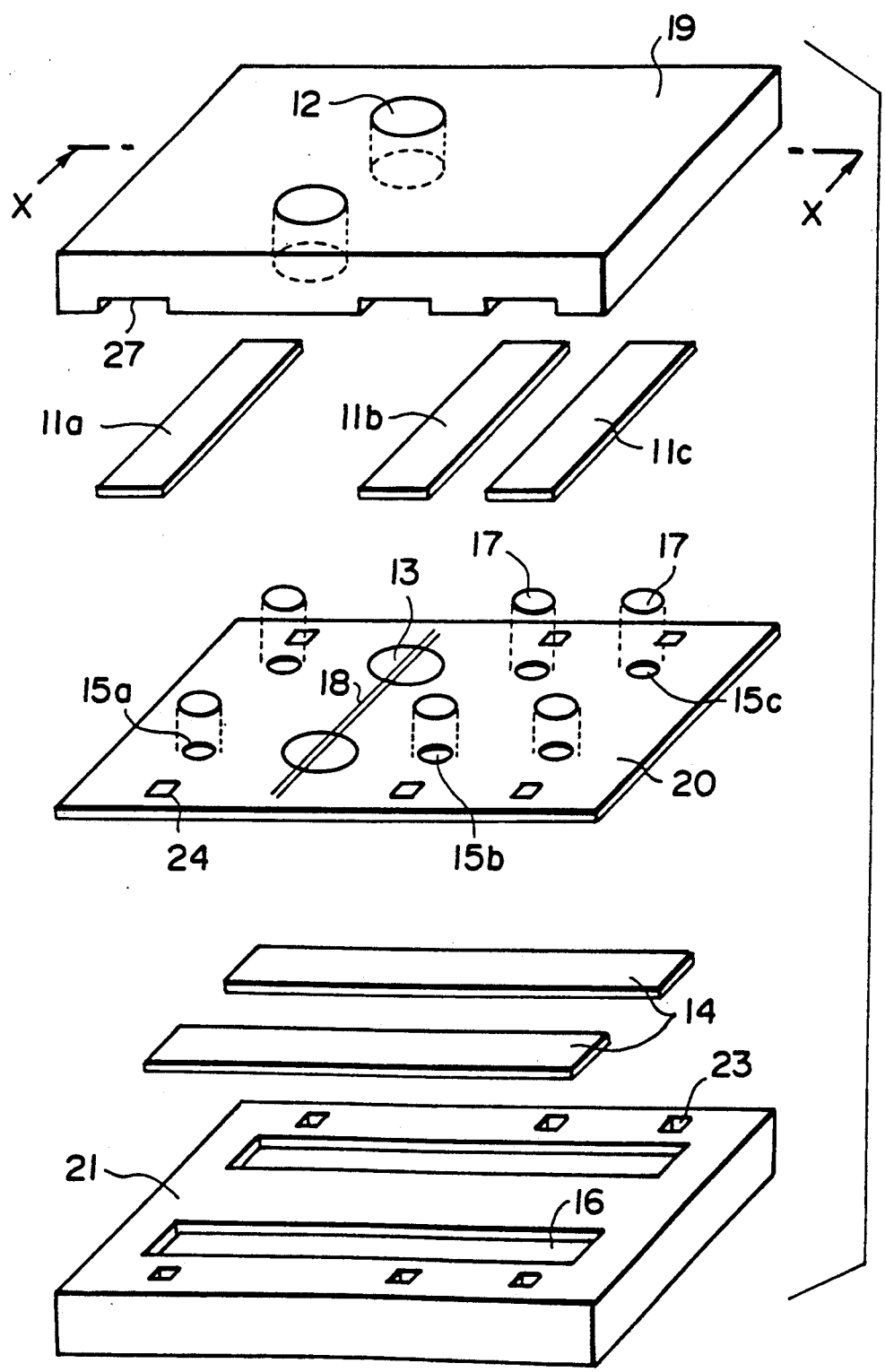
FIG. 1 is a perspective exploded view showing a device for determining ionic activity values in accordance with the present invention.

An embodiment of a device for determining ionic activity values, in which an ion-selective electrode in accordance with the present invention is used, is shown in FIG. 1. This device comprises:

three sheet-like ion-selective electrode pairs 11a, 11b and 11c each having an ion-selective layer on the lower surface and electric contact areas at both ends thereof;

an upper frame 19 having a pair of liquid spotting apertures 12 through which a test liquid and a reference liquid are respectively spotted and grooves 27 for receiving the ion-selective electrode pairs on a lower surface thereof;

a water-impermeable sheet member 20 which is spaced apart from the ion-selective layers of the ion-selective electrode pairs such that capillary action does not occur therebetween, while facing the lower surfaces of the ion-selective layers of the ion-selective electrode pairs;

four pairs of liquid supplying apertures 13, 15a, 15b and 15c formed in the sheet member 20;

a porous bridge 18 made of a fiber (e.g. polyester fiber) which is fixed to an upper surface of the sheet member 20 and connects a pair of liquid supplying apertures 13 to each other;

a pair of porous members 14 which respectively distribute the test liquid and the reference liquid to the liquid supplying apertures 15a, 15b and 15c; and a lower frame 21 which has a pair of indentations 16 for receiving the respective porous members 14.

Further, three pairs of electrode terminal apertures 23 are formed in the lower frame 21 outside of the indentations 16. Also, three pairs of electrode terminal apertures 24 are formed in the sheet member 20.

Figure 1C:
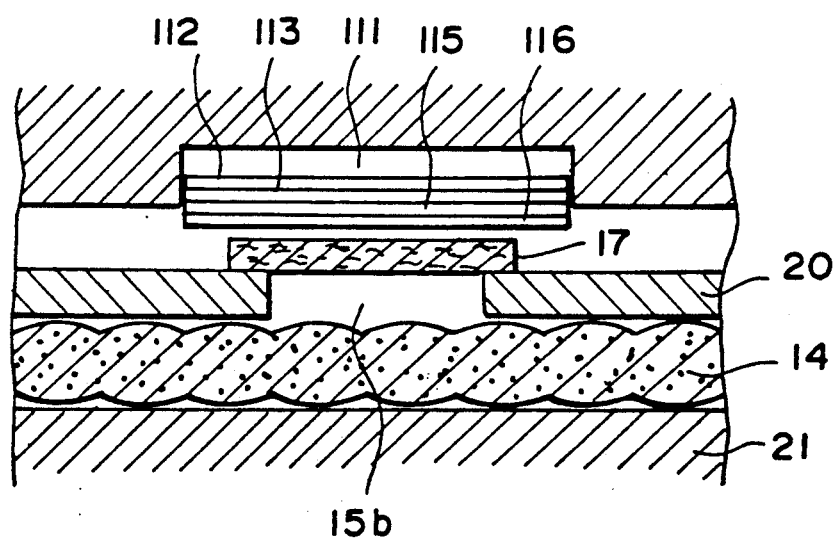
FIG. 1C is a cross sectional view of the electrode 11c and its vicinity shown in the same manner as FIG. 1B.

The three ion-selective electrode pairs 11a, 11b and 11c are selective for sodium ion, potassium ion and chloride ion, respectively. As shown in FIG. 1B, each ion-selective pair comprises a polyethylene-terephthalate film support 111 having a thickness of about 0.2 mm, a silver layer 112, a silver chloride layer 113, an electrolyte layer 114 (which is omitted in the chloride ion-selective electrode 11c) and an ion-selective layer 115 mounted in this order. The chloride ion-selective electrode has further a layer 116 of a material having contact angle of at least 90° C. with water, as shown in FIG. 1C. Each ion-selective electrode pair has a rectangular shape having a length of 24 mm and a width of 5 mm.

The sheet member 20 is spaced from the electrode pairs 11a, 11b and 11c by about 0.3 mm. A circular patch 17 made of a non-woven cloth having a diameter of 2.5 mm is placed on each of the liquid supplying apertures 15a, 15b and 15c.

When predetermined amounts of a test liquid and reference liquid are spotted in the respective liquid spotting apertures, the test liquid and the reference liquid penetrate into the respective porous members 14 and are then supplied to the surfaces of the ion-selective electrodes 11a, 11b and 11c through the liquid supplying apertures 15a, 15b and 15c and the patches 17. On the other hand, both liquids penetrate into the bridge 18 and come into contact with each other near the center of the bridge 18, thereby achieving a liquid junction. Accordingly, a potential difference appears across each pair of ion-selective electrodes. Therefore, a potentiometer is connected to the electric contact areas at both ends of the electrode pairs where the silver layer 112 is exposed.

For example, when the three ion-selective electrode pairs are respectively selective for sodium, potassium and chloride ions, the values of activity of the respective ions are determined at the corresponding ion-selective electrode pairs. If the relationship between the potential drop across the electrode pair and the concentration of each ion were known beforehand, the concentration of each ion could be determined based on the measured potential difference. The amounts of the test liquid and reference liquid to be spotted are selected according to the volume of the liquid receiving means such as the porous members and the liquid supplying apertures.

EXAMPLE 1

A sheet-like silver/silver chloride electrode was formed as described in U.S. Pat. No. 4,555,274. Namely, on a polyethylene terephthalate film having a thickness of 180 μm, a silver layer having a thickness of about 800 nm was vapor-deposited and the film was cut into pieces 24 mm in width. A groove was formed in the silver layer along the longitudinal center line by using a cutter. Both edge portions (3 mm each in width) of the silver layer were coated with a masking agent. After drying the masking agent, the film was subjected to a halogenation treatment in which the following solution was used to form silver chloride on the surface of the silver layer.

| | |
|---|---|
| hydrochloric acid (36%) | 5 g |
| potassium dichromate | 7 g |
| water | 1 l |

After being treated with the above-mentioned solution for 60 sec. at 35° C., the film was washed with water and dried. Then, the whole surface of the silver chloride layer and the groove was coated with a solution having the following composition (a) such that a chloride ion-selective layer having a thickness of 11 μm was formed after drying.

| (a) | |
|---|---|
| polyvinyl butyral ("2000-L" produced by Denki Kagaku Kogyo K.K.) | 1.0 g |
| trioctylmethylammonium chloride ("Aliquot 336" produced by Aldrich Chemical) | 1.0 g |
| 10% methylethylketon solution of surfactant KF-945 (produced by Shinetsu Kagaku Kogyo K.K.) KF-945 (product name): | 0.4 ml |

$$CH_3-Si(CH_3)_2-O\text{-}[Si(CH_3)_2-O]_m\text{-}[Si(CH_3)(R')-O]_n\text{-}Si(CH_3)_3$$

where $R' = (CH_2)_3-O-(CH_2CH_2O)_P-R$ m + n = 32, P = 5, R = H, n = 4

| ethanol | 7.0 g |
|---|---|

Further, on the ion-selective layer, 0.1% cyclohexane solution of paraffin (m.p. 68°–70° C.) was coated with a thickness of about 0.1 μm and dried. Thereafter, the mask layers coated on the edge portions were peeled off to expose the silver layer.

The electrode film thus formed was cut into pieces having a width of 5 mm and a length of 24 mm such that the groove lies in the longitudinal center thereof. Then, together with the sheet-like sodium ion-selective electrode and potassium ion-selective electrode having the same size formed by known methods, the electrode film was incorporated in a device like that shown in FIG. 1 for determining ionic activity levels. By using this device in a "FUJI DRYCHEM 800 ANALYZER" produced by Fuji Photo Film Co., Ltd., potentiometry was conducted. For this example, "Moni-Trol I" (produced by American Dade) was used as a test liquid, while Fuji Drychem Electrolyte Reference Liquid was used as a reference liquid. The potentiometry results are shown in Table 1. Each potential value shown is an average of 20 measurements.

Also, for comparison, the potential drop across the electrode pair was measured by using a chloride ion-selective electrode which was formed in the same manner as Example 1 except for omitting the coating with the paraffin solution.

As shown in Table 1, the chloride ion concentration level can be measured very accurately with a coefficient of variation of less than 2% in the chloride ion-selective electrode in accordance with the present invention. When compared to the electrode of the present invention, the electrode of the comparative example exhibits a remarkably great standard deviation or coefficient of variation.

After the measurement of the potential drop, the device was broken up to observe the traces of the liquids which had been in contact with the surface of the chloride ion-selective electrode. The diameter of each contact area was measured and the results are also shown in Table 1. It is clear that the difference between the maximum and minimum values of the contact area in the chloride ion-selective electrode in accordance with the present invention is smaller than that of the comparative example.

TABLE 1

| | EXAMPLE 1 | COMPARATIVE EXAMPLE |
|---|---|---|
| Average (meq/l) | 105 | 101 |
| Standard Deviation (meq/l) | 2.03 | 9.48 |
| Coefficient of Variation (%) | 1.94 | 9.40 |
| Spot Diameter (mm) | | |
| Test Liquid | | |
| Average | 3.0 | 3.5 |
| Min | 2.5 | 2.5 |
| Max | 4.0 | 5.0 |
| Reference Liquid | | |
| Average | 2.8 | 2.9 |
| Min | 2.5 | 2.3 |
| Max | 3.5 | 4.0 |

EXAMPLE 2

A chloride ion-selective electrode was formed in the same manner as Example 1 except that the following liquid composition (a') was used in place of the liquid composition (a), and potentiometry was conducted in the same manner as in Example 1.

| (a') | |
|---|---|
| vinyl chloride-vinyl acetate copolymer ratio of polymerization 90:10 ("VYNS" produced by Union Carbide) | 1.0 g |
| trioctylmethylammonium chloride ("Aliquot 336" produced by Aldrich Chemical Company) | 0.6 g |

-continued

| (a') | |
|---|---|
| ethanol | 7.0 g |

Like Example 1, the electrode potential was reproduced well.

EXAMPLE 3

A chloride ion-selective electrode was formed in the same manner as in Example 1 except that a behenic acid 1% cyclohexane solution was used in place of the 0.1% paraffin solution to form a layer having a thickness of about 0.7 μm. The potential drop and the diameter of the liquid contact area were measured in the same manner as in Example 1. The results are shown in Table 2.

EXAMPLE 4

A chloride ion-selective electrode was formed in the same manner as in Example 1 except that a 1-eicosanol 1.5% cyclohexane solution was used in place of the 0.1% paraffin solution to form a layer having a thickness of about 1 μm. The potential drop and the diameter of the liquid contact area were measured in the same manner as in Example 1. The results are shown in Table 2.

TABLE 2

| | EXAMPLE 3 | EXAMPLE 4 |
|---|---|---|
| Average (meq/l) | 96 | 99 |
| Standard Deviation (meq/l) | 1.25 | 3.96 |
| Coefficient of Variation (%) | 1.31 | 4.00 |
| Spot Diameter (mm) | | |
| Test Liquid | | |
| Average | 3.0 | 2.5 |
| Min | 2.5 | 2.5 |
| Max | 4.0 | 2.6 |
| Reference Liquid | | |
| Average | 3.0 | 2.8 |
| Min | 2.5 | 2.5 |
| Max | 4.0 | 3.8 |

As can be seen from Table 2, the chloride ion-selective electrode in accordance with the present invention exhibits a coefficient of variation of less than 4% in the measurement of chloride ion concentration.

I claim:

1. An ion-selective electrode comprising a non-conductive support, a sheet inner reference electrode formed on said support, said inner reference electrode comprising a conductive metal layer mounted on said support, and a layer containing a water-insoluble salt of said metal which layer is mounted on said conductive metal layer, a halide ion-selective layer formed on said inner reference electrode, and a material which forms a contact angle of at least 90° with water, a surface of said ion-selective layer being covered with said material.

2. An ion-selective electrode as defined in claim 1 in which said halide is chloride.

3. An ion-selective electrode as defined in claim 1 in which said material is selected from a group consisting of higher hydrocarbons, fatty acids, higher alcohols, perfluoro fatty acids and polysiloxane compounds.

4. An ion-selective electrode as defined in claim 1 in which said material is selected from a group consisting of paraffin, vaseline, stearic acid, palmitic acid, behenic acid, 2-pentadecanoic acid and 1-eicosanol.

5. An ion-selective electrode as defined in claim 1 in which said material has a thickness falling within the range of about 0.01 μm to about 2 μm.

6. A device for determining ionic activity level comprising an ion-selective electrode pair, a first porous member for supplying a test liquid to a first electrode of said ion-selective electrode pair, a second porous member for supplying a reference liquid to a second electrode of said ion-selective electrode pair, a porous bridge for connecting said liquids so that an electric current will flow through said test liquid and said reference liquid, respectively supplied to said first and second electrodes, and a material which forms a contact angle of at least 90° with water, said material covering a surface of at least one of said electrodes and wherein at least one of said electrodes is a halide ion-selective electrode.

7. A device for determining ionic activity level as defined in claim 6 in which said halide is chloride.

* * * * *